US006261790B1

(12) United States Patent
O'Rourke

(10) Patent No.: US 6,261,790 B1
(45) Date of Patent: Jul. 17, 2001

(54) MONOCLONAL ANTIBODIES AND ANTIBODY COCKTAIL FOR DETECTION OF PRION PROTEIN AS AN INDICATION OF TRANSMISSIBLE SPONGIFORM ENCEPHALOPATHIES

(75) Inventor: Katherine I. O'Rourke, Albion, WA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/353,348

(22) Filed: Jul. 15, 1999

(51) Int. Cl.[7] .......................... A61K 49/00; G01N 33/53; G01N 33/567; C07K 16/00

(52) U.S. Cl. ...................... 435/7.72; 424/9.1; 424/130.1; 424/139.1; 424/141.1; 424/145.1; 424/152.1; 435/7.1; 435/70.1; 435/70.21; 436/503; 436/518; 436/547; 436/548; 530/388.1

(58) Field of Search ................................ 424/9.1, 130.1, 424/139.1, 141.1, 145.1, 152.1; 435/7.1, 7.72, 70.1, 70.21; 436/503, 518, 547, 548; 530/388.1

(56) References Cited

U.S. PATENT DOCUMENTS

| | | | |
|---|---|---|---|
| 4,806,627 | 2/1989 | Wisniewski et al. ................. | 530/387 |
| 5,565,186 | 10/1996 | Prusiner et al. . | |
| 5,773,572 | 6/1998 | Fishleigh et al. ..................... | 530/324 |
| 5,846,533 | 12/1998 | Prusiner et al. . | |

FOREIGN PATENT DOCUMENTS

| | | | |
|---|---|---|---|
| 9919360 | 4/1999 | (WO) ............................ | C07K/16/00 |

OTHER PUBLICATIONS

Horiuchi et al, "A cellular form of prion protein (PrPc) exists in many non–neuronal tissues of sheep", Journal of General Virology, vol. 76, pp. 2583–2587, 1995.*

P. Brown et a., "Diagnosis of Creutzfeldt–Jakob Disease by Western Blot Identification of Marker Protein in Human Brain Tissue," *The New England Journal of Medicine*(1986) pp. 547–551 vol. 314(9).

S. Harmeyer et al., "Synthetic peptide vaccines yield monoclonal antibodies to cellular and pathological prion proteins of ruminants," *Journal of General Virology* (1998) pp. 937–945 vol. 79.

R.A. Williamson et al., "Mapping the Prion Protein Using Recombinant Antibodies," *Journal of Virology* (1998) pp. 9413–9418 vol. 72(11).

K.I. O'Rourke, T.V. Baszler, S.M. Parish, and D.P. Knowles, "Preclinical Detection of PrPSc in Nictitating Membrane Lymphoid Tissue of Sheep," The Veterinary Record 142:489–491 (1998).

K.I. O'Rourke, T.V. Baszler, J.M. Miller, T.R. Spraker, I. Sadler–Riggleman and D.P. Knowles, "Monoclonal Antibody F89/160.1.5 Defines a Conserved Epitope on the Ruminant Prion Protein," Journal of Clinical Microbiology 36(6):1750–1755 (1998).

W. Goldmann, T. Martin, J. Foster, S. Hughes, G. Smith, K. Hughes, M. Dawson and N. Hunter, "Novel Polymorphisms in the Carpine PrP Gene: a Condon 142 Mutation Associated with Scrapie Incubation Period," Journal of General Virology 77:2885–2891 (1996).

A. Bossers, B.E.C. Schreuder, I.H. Muileman, P.B.G.M. Belt, and M.A. Smits, "PrP Genotype Contributes to Determining Survival Times of Sheep with Natural Scrapie," Journal of General Virology 77:2669–2673 (1996).

W.J. Hadlow, R.C. Kennedy & R.E. Race, "Natural Infection of Suffolk Sheep with Scrapie Virus," Journal of Infectious Diseases 146(5):657–664 (1982).

M. Haritani, Y.I. Spencer & G.A.H. Wells, "Hydrated Autoclave Pretreatment Enhancement of Prion Protein Immunoreactivity in Formalin–fixed Bovine Spongiform Encephalopathy–Affected Brain," Acta Neuropathol 87:86–90 (1994).

A.F. Hill, M. Zeidler, J. Ironside & J. Collinge, "Diagnosis of New Variant Creutzfeldt–Jakob Disease by Tonsil Biopsy," The Lancet 349:99–100 (Jan. 1997).

K.I. O'Rourke et al., "PrP Genotypes and Experimental Scrapie in Orally Inoculated Suffolk Sheep in the United States," Journal of General Virology 78:975–978 (1997).

Y. Ikegami, M. Ito, H. Isomura, E. Momotani, K. Sasaki, Y. Muramatsu, N. Ishiguro & M. Shinagawa, "Pre–clinical and Clinical Diagnosis of Scrapie by Detection of PrP Protein in Tissues of Sheep," The Veterinary Record 128:271–275 (1991).

R.J. Kascsak, R. Fersko, D. Pulgiano, R. Rubinstein & R.I. Carp, "Immunodiagnosis of Prion Disease," Immunological Investigations 26(1&2):259–268 (1997).

(List continued on next page.)

Primary Examiner—Rodney P Swartz
(74) Attorney, Agent, or Firm—Margaret A. Connor; M. Howard Silverstein; John D. Fado

(57) ABSTRACT

Methods to detect prion or PrP-Sc protein as an indication of transmissible spongiform encephalopathies (TSEs) are described. In one aspect, the invention is directed to monoclonal antibodies that specifically bind a conserved epitope of prion proteins and use of the antibodies in immunoassays to detect PrP-Sc, in fixed or unfixed tissue, as an indication of the presence of TSE infection. In another aspect, the invention is directed to a monoclonal antibody cocktail having the monoclonal antibody in combination with a second monoclonal antibody which specifically binds to a second conserved epitope of prion proteins. One or both monoclonal antibodies of the cocktail can recognize epitopes found in all mammalian species in which a natural TSE has been reported and in a number of closely related species. Thus, the antibody cocktail provides high sensitivity, defined specificity, and broad reactivity to PrP proteins in spite of interspecies and intraspecies variation of species such as ruminant livestock, cats, mink, humans, and non-human primates.

20 Claims, No Drawings

OTHER PUBLICATIONS

J.M. Miller, A.L. Jenny, W.D. Taylor, R.F. Marsh, R. Rubenstein & R.E. Race "Immunochistochemical Detection of Prion Protein in Sheep with Scrapie," J Vet Diagn Invest 5:309–316 (1993).

J.M. Miller et al., "Detection of Prion Protein in Formalin-Fixed Brain by Hydrated Autoclaving Immunohistochemistry for the Diagnosis of Scrapie in Sheep," J Vet Diagn Invest 6:366–368 (1994).

Y. Muramatsu, A. Onodera, M. Horiuchi, N. Ishiguro & M. Shinagawa, "Detection of $PrP^{Sc}$ in Sheep at the Preclinical Stage of Scrapie and its Significance for Diagnosis of Insidious Infection," Archives of Virology 134:427–432 (1993).

R. Race, D. Ernst, A. Jenny, W. Taylor, D. Sutton & B. Caughey, "Diagnostic Implications of Detection of Proteinase K–Resistant Protein in Spleen, Lymph Nodes, and Brain in Sheep," Am J Vet Res 53(6):883–889 (1992).

B.E.C. Schreuder, L.J.M van Keulen, M.E.W. Vromans, J.P.M. Langeveld & M.A. Smits "Preclinical Test for Prion Diseases," Nature 381:563 (1996).

L.J.M. van Keulen, B.E.C. Schreuder, R.H. Meloen, G. Mooij–Harkes, M.E.W. Vromans & J.P.M. Langeveld, "Immunohistochemical Detection of Prion Protein in Lymphoid Tissues of Sheep with Natural Scrapie," Journal of Clinical Microbiology 34(5):1228–1231 (1996).

L.J.M. van Keulen, B.E.C. Schreuder, R.H. Meloen, M. Poelen–Van Den Berg, G. Mooij–Harkes, M.E.W. Vromans & J.P.M. Langeveld, "Immunohistochemical Detection and Localization of Prion Protein in Brain Tissue of Sheep with Natural Scrapie," Vet Pathol 32:299–308 (1995).

* cited by examiner

MONOCLONAL ANTIBODIES AND ANTIBODY COCKTAIL FOR DETECTION OF PRION PROTEIN AS AN INDICATION OF TRANSMISSIBLE SPONGIFORM ENCEPHALOPATHIES

BACKGROUND OF THE INVENTION

1. Field of the Invention

The present invention relates to detection of prion protein (also denoted as PrP-Sc protein) as an indicator of transmissible spongiform encephalopathies (TSEs). In particular, the invention relates to (a) monoclonal antibodies that specifically bind a conserved epitope of prion proteins, and (b) monoclonal antibody cocktail having the monoclonal antibody in combination with a second monoclonal antibody which specifically binds to a second conserved epitope of prion proteins. The new antibodies and antibody cocktail are useful in immunoassays to detect prion proteins in ruminants and other species in which TSEs occur naturally or in related species potentially exposed to TSEs.

2. Description of the Art

Transmissible spongiform encephalopathies (TSEs) are a heterogeneous group of fatal neurodegenerative disorders that occur in humans, ruminant herbivores, mink, and cats. Sheep scrapie is the prototype of this group. TSEs are characterized by deposition of prion proteins (also denoted as PrP-Scrapie or PrP-Sc), the infectious form of the proteins, in the central nervous system of affected individuals. Prions have been defined as small proteinaceous infectious particles which resist inactivation by procedures that modify nucleic acids. The term "prion" is a contraction of the words "protein" and "infection," and prions are comprised largely if not exclusively of PrP-Sc molecules encoded by a PrP gene. Prion diseases are often called spongiform encephalopathies because of the post mortem microscopic or histopathologic appearance of the brain of an infected animal with large vacuoles in the cortex and cerebellum. Prion proteins are insoluble, protease-resistant glycoproteins resulting from post translational modification of normal mammalian glycoproteins (PrP-Cellular or PrP-C), and deposition of the PrP-Sc protein, the abnormal isoform of PrP-C sialoglycoprotein, in the central nervous system is a reliable marker of TSE infection.

The most widely studied TSEs in food-producing animals include scrapie in sheep and goats, bovine spongiform encephalopathy (BSE) in cattle (also known as "Mad Cow" disease), and chronic wasting disease (CWD) in mule deer and elk. Other TSEs in animals included transmissible mink encephalopathy (TME) in mink and feline spongiform encephalopathy (FSE) of domestic and nondomestic cats. Most recently, a TSE of non-human primates held in zoos in France was reported; this disease probably originated from BSE (Bons et al., *Proceedings of the National Academy of Sciences of the United States of America* 96:4046–4051 (1999)). Prion diseases of humans have also been identified. These include: Creutzfeldt-Jakob Disease (CJD); Gerstmann-Straussler-Scheinker Syndrome (GSS); Fatal Familial Insomnia (FFI), and Kuru.

The transmissible agent in these diseases remains controversial. However, as noted above, an insoluble isoform (prion or PrP-Sc) of a mammalian sialoglycoprotein (PrP-Cellular or PrP-C) is a major component in infectious material. It appears that the scrapie isoform of the prion protein (PrP-Sc) is necessary for both the transmission and pathogenesis of the transmissible neurodegenerative diseases of animals and humans (see S. B. Prusiner, *Science* 252:1515–1522 (1991) and S. B. Prusiner, *Proceedings of the National Academy of Sciences of the United States of America* 95:13363–13383 (1998)). A leading hypothesis is that prion diseases result from the conversion of PrP-C to PrP-Sc by a nucleation or polymerization event.

The occurrence of novel transmissible spongiform encephalopathies in cattle in the United Kingdom and Europe and in mule deer and elk in parts of the United States has emphasized the need for reliable diagnostic tests. Further, the epizootic of a TSE in cattle and its postulated relationship to a new variant of human Creutzfeldt Jakob Disease (M. E. Bruce et al., *Nature* 389:498–501 (1997) and A. F. Hill et al., *Nature* 389:448–450 (1997)) have increased public and scientific awareness of these relatively rare disorders, and have highlighted the need for preclinical detection of TSEs. Although no cases of BSE have been detected in the United States, sensitive immunohistochemical techniques and preclinical detection methods are basic for detection, surveillance, and control of TSEs.

Prion diseases can have a long incubation period. For example, in sheep it can take 3 to 5 years from the time when an animal becomes infected until it first shows disease signs. In bovine spongiform encephalopathy (BSE) it can take two to eight years from the time when an animal becomes infected until it first shows disease signs. Infected animals and humans have neither a disease-specific immune response nor consistent biochemical, hematological and gross pathological abnormalities. The early diagnosis of transmissible spongiform encephalopathies can therefore be dependent on the appearance of clinical signs, electroencephalography, or the invasive method of taking brain biopsies. Confirmation of TSEs is accomplished by postmortem microscopic or histological examination of brain tissue of suspected cases. Postmortem histopathologic diagnosis of the ruminant TSEs is based on the appearance of neuronal vacuolation, spongiform changes, gliosis, and astrocytosis. However, these can vary in intensity and anatomic location depending on the host species, the individuals, host genetics, stage of disease, and infectious source. Thus, diagnosis by histopathology alone may be equivocal in early cases and usually not possible in autolyzed tissue.

Deposition of prion protein (PrP-Sc) in the central nervous system is a reliable marker for the TSEs. Immunohistochemical detection of PrP-Sc is therefore an important adjunct to histopathology in diagnosis, surveillance, and control of TSEs. Monoclonal antibody 263K 3F4 (U.S. Pat. No. 4,806,627) detects PrP-Sc in hamsters and humans, and has received widespread use in diagnostic assays and pathogenesis studies of human TSEs. A major disadvantage is that it fails to react with PrP from sheep and cattle (R. J. Kascsak et al., *Immunological Investigations* 26:259–268 (1997)). Rabbit antisera reactive with ruminant PrP-Sc has the disadvantages that it cannot be standardized for widespread use due to limitations in quantity and specificity. Monoclonal antibodies are preferable to rabbit antisera because quantities are not limited and specificity can be precisely defined at the level of a single epitope. This specificity, however, can be a drawback in species with polymorphic PrP genes. A single base change resulting in an amino acid substitution in the epitope can eliminate binding by the antibody. The human PrP gene has at least 18 pathogenic mutations leading to inherited prion disease (J. Collinge et al., *Philos. Trans. Royal Soc. Lond.* [*Biol.*] 343:371–378 (1994)) and a number of non pathogenic mutations, one of which (codon 129) which is associated with predisposition to iatrogenic, sporadic and variant CJD (J. Collinge et al., *Lancet*

337:1441–1442 (1991); M. S. Palmer et al., *Nature* 352:340–342 (1991); M. Zeidler et al., *Lancet* 350:668 (1997)). M. Horiuchi et al. (*Journal of General Virology* 76:2583–2587 (1995)) describe a panel of synthetic peptides that generated monoclonal and polyclonal antibodies reactive with the PrP-Cellular, (the non-disease-related protein) in immunoblots of selected sheep and cattle tissue. They did not report effectiveness for detecting the disease-related isoform, PrP-Sc. Additionally, they did not they report effectiveness in detecting either PrP-C or PrP-Sc in formalin fixed tissues.

Post mortem diagnosis of prion diseases is made using histologic and immunohistochemical assays on brain tissue. Ante-mortem testing in humans with suspected CJD is performed by immunohistochemical and histologic examination of brain biopsies. In addition, individuals with the new variant of CJD related to exposure to BSE have PrP-Sc accumulations in lymphoid tissues (A. F. Hill et al., *Lancet* 349:99 (1997)). The presence of PrP-Sc in lymphoid tissue differentiates variant CJD from sporadic or familial disease. Because brain biopsy in ruminant animals is not feasible, an alternative approach, based on W. J. Hadlow et al.'s observation (*The Journal of Infectious Diseases* 146:657–664 (1982)), has been to biopsy selected lymph nodes. Hadlow et al. demonstrated that infectivity was detectable in certain lymph nodes (retropharyngeal, tonsil, mesenteric, prescapular, bronchial-mediastinal, and spleen) and the lymphoid tissue in the intestine of scrapie-infected sheep. Hadlow's studies, carried out before the discovery of the prion protein, detected infectivity by mouse inoculation. Race et al. (*American Journal of Veterinary Research* 53:883–889 (1992)), Ikegami et al. (*Veterinary Record* 128:271–275 (1991)), and van Keulen et al. (*Journal of Clinical Microbiology* 34:1228–1231 (1996)) performed similar surveys by Western immunoblots or immunohistochemical assay of selected lymph nodes using polyclonal antisera. Biopsy of tonsillar tissue in humans with clinical signs of variant CJD is a less invasive procedure than brain biopsy and immunoassays of lymphoid tissue can be used to diagnose variant CJD and to differentiate it from familial, iatrogenic and sporadic CJD. In ruminant livestock, however, the major disadvantages to tonsil or lymphoid tissue sampling include the following: sampling of these internal tissues requires expensive invasive methods including general anesthesia with its concomitant risks and recovery period; lymphoid tissues of sheep are often infected with a bacteria, *Corynebacterium pseudotuberculosis*, which destroys the architecture of the node and limits its use in these assays; and tonsillar tissue traps environmental antigens, including fungal antigens, some of the which cross react with PrP-Sc, giving equivocal or false positive immunohistochemical reactions which must be resolved by technically demanding Western blot analysis. More recently, O'Rourke et al. (*The Veterinary Record*, May 2, 1998, pages 489–491) described a non-invasive diagnostic assay for preclinical detection of PrP-Sc in sheep using nictitating membrane (third eyelid) lymphoid tissue.

Current U.S. Federal regulations require the destruction of scrapie-infected sheep, and some states require destruction of all sheep within a flock born within a 60-day period following delivery of a lamb by a ewe subsequently diagnosed with scrapie. Such eradication procedures are very costly to the industry. In addition, American sheep are large, meaty, and fast growing. Many foreign countries are anxious to purchase American sheep for genetic purposes, but are prevented from doing so because of the presence of scrapie.

The BSE epidemic in the United Kingdom and the European community has cost producers and consumers in direct livestock losses and indirect loss of markets for beef and beef by-products, including economically important pharmaceutical products. Sheep and beef producing countries around the world are conducting costly surveillance and quarantine programs to maintain their status as BSE-free. Most importantly, data from several scientific lines of inquiry have provided strong evidence that BSE has infected humans in Great Britain. The scope of this new disease has yet to be determined.

What is needed is a practical immunoassay reagent system suitable for detection of PrP-Sc in tissues from humans, food producing animals, companion animals, and nondomestic animals in zoos. The assay reagents must be suitable for detection of PrP-Sc in individuals of varying PrP genotypes within each species; and sensitive and specific when used in a variety of standard laboratory protocols.

SUMMARY OF THE INVENTION

The present invention relates to methods for detection of prion or PrP-Sc proteins as an indication of transmissible spongiform encephalopathies. In one embodiment, the invention comprises monoclonal antibodies that specifically bind a conserved epitope on prion proteins identified as Gln-Tyr-Gln-Arg-Glu-Ser SEQ ID NO: 1, and immunoassay methods using the antibodies, including immunohistochemistry assays and Western blotting. The antibodies are useful to detect PrP-Sc in fixed or unfixed tissue, as an indication of the presence of TSE infection.

In a second embodiment, the invention comprises a monoclonal antibody cocktail having the aforenamed monoclonal antibody in combination with a second monoclonal antibody which specifically binds to a second conserved epitope on prion proteins, designated as Ile-His-Phe-Gly SEQ ID NO: 2. The latter antibody is described in U.S. Pat. No. 6,165,784. Surprisingly, we have found the combination (herein denoted as monoclonal antibody cocktail) of the antibodies to nonoverlapping, separate epitopes provides the optimum combination of high sensitivity, defined specificity, and broad reactivity to PrP proteins in spite of interspecies and intraspecies variation. One or both monoclonal antibodies in this cocktail can recognize epitopes found in all mammalian species in which a natural TSE has been reported and in a number of closely related species.

The invention further includes immunoassay methods using the antibodies of the first embodiment and antibody cocktail, including immunohistochemistry assays, Western immunoblots, and dot blots.

The antibody of the first embodiment and the antibody cocktail of the invention can be used in a non-invasive diagnostic assay using third eyelid lymphoid tissue to detect PrP-Sc as described in U.S. Pat. No. 6,165,784. The nictitating membrane or third eyelid (*palpebra tertia*) of ruminant animals consists of a cartilaginous sheet with superficial lymphoid follicles and a seromucinous secretory gland beneath the conjunctiva of the bulbar surface. Ruminant animals including sheep, goats, mule deer, elk and cattle have third eyelids. A sample of nictitating membrane-associated lymphoid tissue can be readily collected by everting the third eyelid. Typically two clusters of lymphoid tissue are visualized superior to the more pale glandular tissue. Biopsy of the lymphoid nodule can be performed using only local anesthetic. The collected tissue sample is then subjected to immunohistochemical or other protein-detecting methods which are capable of detecting prion or PrP-Sc, if present in the tissue. Thus, the third eyelid represents an easily obtainable specimen for testing tissue from live animals or from animals sampled at slaughter. This detection method provides a much needed practical method for early detection of PrP-Sc and provides a means for preclinical diagnosis of TSEs.

In accordance with this discovery, it is an object of the invention to provide monoclonal antibodies that recognize a conserved epitope of prion protein and a pan-specific antibody cocktail that comprises monoclonal antibodies to nonoverlapping, separate epitopes on prion proteins of the species in which TSEs occur naturally (humans, cattle, sheep, goats, deer, elk, mink, domestic and nondomestic cats, several species of nondomestic ruminant animals and many species of non-human primates housed in zoos) and other closely related species potentially exposed to TSE infection. The antibodies detect PrP-Sc in fixed, treated tissue as an indication of the presence of TSE infection, and provide a sensitive reagent mixture for diagnosis of TSEs. These monoclonal antibody reagents to conserved epitopes on PrP-Sc provide specific, reliable, and flexible tools for the accurate diagnosis of TSE. Uses of the antibodies include as reagents for standardized diagnostic testing and comparative pathology studies.

It is a further object of the invention to provide methods for detection of prion or PrP-Sc as a marker for TSEs, including preclinical detection of infected live animals, and postmortem detection methods.

Another object of the invention is the provision of non-invasive diagnostic assays based on biopsy of third eyelid lymphoid tissue and detection of PrP-Sc in situ as a practical method for early detection of PrP-Sc.

A still further object comprises immunoassay methods useful in diagnostic and pathogenesis studies of TSE in ruminants and humans, and useful for detection, surveillance, and control of TSEs.

Other objects and advantages of the invention will become readily apparent from the ensuing description.

DETAILED DESCRIPTION OF THE INVENTION

In a first embodiment, the invention comprises monoclonal antibodies that specifically bind a conserved carboxyl epitope on prion proteins identified as Gln-Tyr-Gln-Arg-Glu-Ser SEQ ID NO: 1. The monoclonal antibodies bind an epitope on the PrP proteins in fixed or frozen tissue that has been treated to unmask the epitope to PrP-Sc and eliminate the availability of the corresponding epitope of PrP-C. For purposes of this invention, the term prion or PrP-Sc is defined as the disease-related protein that is a marker of TSEs. Because the antibodies detect PrP-Sc in fixed, treated tissue or in frozen tissue pretreated with proteinase K to degrade PrP-C as an indication of the presence of TSE infection, they provide a sensitive reagent for diagnosis of TSEs.

Antibodies of the invention were obtained as described in Example 2, below. In brief, a peptide was synthesized representing ovine residues 217–233 (bovine residues 225–241) Cys-Ile-Thr-Gln-Tyr-Gln-Arg-Glu-Ser-Gln-Ala-Tyr-Tyr-Gln-Arg-Gly-Ala SEQ ID NO: 3, and it was coupled to maleimide-activated KLH for use as an immunogen. Antisera and monoclonal antibodies from inoculated mice were screened for reactivity to recombinant sheep PrP to select cross-reacting antibodies. These antibodies were then shown to be reactive with PrP-Sc in formalin fixed, hydrated autoclaved tissue of sheep, mule deer and elk, and cattle.

For purposes of this invention, monoclonal antibodies that specifically bind the conserved epitope of PrP-Sc encompassed by this invention are those which are specific for the epitope of the PrP gene product, comprising the peptide Gln-Tyr-Gln-Arg-Glu-Ser SEQ ID NO: 1, and detect PrP-C in frozen, untreated tissue and PrP-Sc in fixed or frozen, treated tissue. Exemplary of the monoclonal antibodies that bind this conserved epitope in fixed or unfixed, treated tissue is monoclonal antibody F99/97.6.1. The isotype of the antibody is IgG1.

The invention also encompasses immunoassay methods using the antibodies, including immunohistochemistry assays and Western blotting. The antibodies are useful to detect PrP-Sc in fixed or unfixed tissue, as an indication of the presence of TSE infection.

In a second embodiment, the invention comprises a monoclonal antibody cocktail having the aforenamed monoclonal antibody in combination with a second monoclonal antibody which specifically binds to a second conserved epitope of the PrP gene product in sheep, mule deer and elk, and cattle, designated as Ile-His-Phe-Gly SEQ ID NO: 2. These monoclonal antibodies are described in detail in U.S. Pat. No. 6,165,784, which is incorporated herein in its entirety by reference. This epitope was further identified as comprising amino acids 142–145 of the ovine (sheep) PrP gene product, which are identical to amino acids 142–145 of the cervid (mule deer and Rocky Mountain elk) PrP gene product and amino acids 150–153 of the bovine PrP gene product. The antibodies have the further property that they detect the unmasked epitope to PrP-Sc protein in fixed or frozen tissue, and thus they are useful as reagent for diagnosis of TSEs in sheep, goats, cattle, mule deer, and elk with naturally occurring TSE. Presence of PrP-Sc indicates the scrapie-, bovine encephalopathy- or chronic wasting disease-infected animals.

Exemplary of the monoclonal antibodies that bind the conserved epitope Ile-His-Phe-Gly SEQ ID NO: 2 of PrP-Sc in fixed or frozen, treated ruminant tissue is monoclonal antibody F89/160.1.5. The isotype of this antibody is IgG1. The immunohistochemical staining pattern of monoclonal antibody F89/160.1.5 was similar to patterns described in the brain of scrapie-affected sheep using polyclonal rabbit antisera to ovine or hamster PrP. Another exemplary monoclonal antibody which specifically binds the epitope to which monoclonal antibody F89/160.1.5 is directed is monoclonal antibody F89/193.1.5.

Genetic variation in goats at an amino acid residue in the epitope of monoclonal antibodies F89/160.1.5 and F89/193.1.5 has been reported (Ile to Met at codon 142) (W. Goldmann et al., *Journal of General Virology* 77:2885–2891 (1996)), and a mutation in the sheep gene at codon 141 (Phe to Leu), which flanks the epitope, has been reported (A. Bossers et al., *Journal of General Virology* 77:2669–2673 (1996)). Although these variations occur only in small subpopulations of these species, the possibility exists that the variations, or other variations not yet identified, may prevent binding of these monoclonal antibodies to the prion protein, and sensitive immunohistochemical techniques and preclinical detection methods for detection, surveillance, and control of TSEs including genetic variants is important.

Surprisingly, we have found the combination (herein denoted as monoclonal antibody cocktail) of the antibodies to these two nonoverlapping, separate epitopes provides the optimum combination of high sensitivity, defined specificity, and broad reactivity to PrP proteins in spite of interspecies and intraspecies variation. The monoclonal antibody cocktail of the invention appears to detect all species and all the known variations in which TSEs naturally occur. The antibodies detect PrP-Sc in unfixed or fixed, treated tissue as an indication of the presence of TSE infection, and provide a sensitive reagent mixture for diagnosis of TSEs. Examination of PrP sequences deposited at GenBank (Table 1) demonstrates that the antibody cocktail will detect epitopes on the PrP gene product of sheep, cattle, humans, deer, elk, mink, domestic cats and 56 species of nondomestic ruminants and nonhuman primates. The antibodies bind nonoverlapping epitopes in formalin fixed tissues, as doubling the concentration of either antibody is less sensitive than combining the antibodies in equal concentration. The antibodies to each epitope and the antibody cocktail detect PrP-Sc in fixed or frozen, treated tissue as an indication of the presence of TSE infection, and provide a sensitive reagent for diagnosis of TSEs. Tissue samples useful for testing for PrP-Sc include third eyelid-associated lymphoid tissue, brain necropsy tissue, lymph node biopsy or necropsy tissue or spleen biopsy or necropsy tissue. The monoclonal antibody forms an antigen-antibody complex and the bound antibody is detected by immunological means such as enzyme-linked immunoabsorbent assay, Western blot assay, dot blot assay, immunodecoration and immunocytochemistry.

Statement of Deposit. The continuous cell line (hybridoma) which produces and secretes monoclonal antibody F99/97.6.1 was deposited on Apr. 6, 1999, with the American Type Culture Collection (ATCC), 10801 University Blvd., Manassas, Va. 20110–2209 USA, under terms of the Budapest Treaty, and has been assigned accession number ATCC HB-12696. The continuous cell line (hybridoma) which produces and secretes monoclonal antibody F89/160.1.5 was deposited on Sep. 24, 1997, with ATCC, under terms of the Budapest Treaty, and has been assigned accession number ATCC HB-12403. The continuous cell line (hybridoma) which produces and secretes monoclonal antibody F89/193.1.5 was deposited on May 25, 1999, with ATCC, under terms of the Budapest Treaty, and has been assigned accession number PTA-114.

TABLE 1

Species in which the PrP gene product contains the epitope(s) Ile-His-Phe-Gly SEQ ID NO:2 and/or Gln-Tyr-Gln-Arg-Glu-Ser SEQ ID NO:1

| | |
|---|---|
| Addax nasomaculatus | Mandrillus sphinx |
| African dwarf goats | Meriones unguiculatus |
| Antilocapra americana | Mus musculus |
| Aotus trivirgatus | Mustela spp (mink) |
| Ateles geoffroyi | Mustela putorius |
| Ateles paniscus x ateles fusciceps | Odocoileus hemionus hemionus |
| Bison bonasus | (mule deer) |
| Bos javanicus | Odocoileus virginianus (white |
| Bos primigenius | tailed deer) |
| Bos taurus (cattle) | Oryctolagus cuniculus |
| Budorcas taxicolor | Ovibos moschatus |
| Callicebus moloch | Ovis aries (domestic sheep), |
| Callithrix jacchus | all reported variants |
| Camelus dromedarius | Pan troglodytes |
| Canis familiaris | Papio Hamadryas |
| Capra hircus (goat), | Pongo pygmaeus |
| both reported variants | Presbytis francoisi |
| Capra ibex nubiana | Saimiri sciureus |
| Cebus apella | Sigmodon fulviventer |
| Cercocebus aterrimus | Sigmodon hispiedis |
| Cercocebus torquatus atys | Sus scrofa |
| Cercopithecus diana | Theropithecus gelada |
| Cercopithecus mona | Tragelaphus strepsiceros |
| Cercopithecus neglectus | Trichosurus vulpecula |
| Cercopithecus patas | |
| Cervus elaphus spp (elk) | |
| Cervus nippon dybowskii | |
| Chlorocebus aethiops | |
| Colobus guereza | |

TABLE 1-continued

Species in which the PrP gene product contains the epitope(s) Ile-His-Phe-Gly SEQ ID NO:2 and/or Gln-Tyr-Gln-Arg-Glu-Ser SEQ ID NO:1

Equus caballus
Equus przewalskii
Felis catus
Gazella subgutturosa
Giraffa camelopardalis
Gorilla gorilla
Hippotragus niger
Homo sapiens (human), all reported variants
Hylobates lar
Hylobates syndactylus
Macaca arctoides
Macaca fascicularis
Macaca fuscata
Macaca mulatta
Macaca nemesttrina
Macaca sylvanus Immunoassay methods using the antibodies are also encompassed by the invention. In brief, to detect PrP-Sc, a tissue sample is obtained from a subject to be tested; the tissue is fixed, for example, by preserving in formalin or paraformaldehyde as known in the art. Next, the fixed tissue section is treated to unmask the epitope to PrP-Sc and eliminate availability of the corresponding epitope of PrP-cellular which is expressed in tissues from normal animals. This can be conveniently carried out by (a) hydrated autoclaving, e.g., by autoclaving hydrated sections in water or buffer at about 121° C. for 20 to 30 minutes, followed by cooling; (b) treatment with 95–99% formic acid for 5 to 30 minutes with or without a subsequent step of hydrated autoclaving, or (c) digestion with trypsin (e.g., 0.1% trypsin for 20 minutes at 37° C. in Tris HCl buffer, pH 7.6). The fixed, treated tissue is contacted with the monoclonal antibody or monoclonal antibody cocktail of the invention in an amount and under conditions effective to bind PrP-Sc protein if present in the tissue. As noted in the examples, incubation of a tissue sample with about 3–5 µg/ml of either of the monoclonal antibodies or with a cocktail of about 3–5 µg/ml of each antibody in a suitable buffer for 30 minutes causes the antibody to be bound to the conserved PrP-Sc epitope. Bound antibody is detected by procedures known in the art. In one aspect, the monoclonal antibody bound to the tissue sections is detected by contacting it with a detectably labeled (enzymatic, radioactive, or fluorescent detection molecules or biotin molecules) anti-mouse immunoglobulin (e.g., IgG1) reagent under conditions such that the labeled anti-mouse immunoglobulin reagent binds to the monoclonal antibody and can subsequently be detected by activity of the enzyme, radioactive, or fluorescent label or by binding of the biotin label to an avidin/streptavidin molecule labeled with enzymatic, radioactive, or fluorescent molecules. In the preferred embodiment, detection is carried out by sequential incubation of the anti-mouse immunoglobulin reagent, e.g. biotinylated anti-mouse IgG, and horseradish-peroxidase labeled streptavidin with intervening washes in buffer, e.g., Tris-HC-Tween 20. An indicator chromogen such as AEC is added to detect the bound antibody.

Alternatively, frozen tissue is homogenized in detergent and treated with proteinase K to eliminate the 35K PrP-C band and reveal the characteristic multiple 28–32K bands of proteinase K-resistant PrP-Sc fragments. Treated proteins are separated on polyacrylamide gels and transferred to filters. The filter is contacted with the monoclonal antibody of the invention or the monoclonal antibody cocktail of the invention in an amount and under conditions effective to bind PrP-Sc protein if present in the tissue. The antibody or antibody cocktail is detected as described above except that the preferred final detection step is with a chemiluminescent substrate.

As discussed above, antibodies of the invention are useful in diagnostic and pathogenesis studies of the TSEs.

EXAMPLES

The following examples are intended only to further illustrate the invention and are not intended to limit the scope of the invention which is defined by the claims.

Example 1

The following example describes a PrP-Sc detection assay using the cocktail of the invention on ovine lymphoid tissue.

Animals tested. Twenty seven sheep of the Suffolk or related black-faced breeds from flocks with no known exposure to scrapie infected ewes were sampled by biopsy of nictitating membrane lymphoid tissue. Forty seven sheep from flocks exposed to scrapie were sampled at necropsy; at a minimum, brain, retropharyngeal lymph node, and tonsil were collected. All tissues were negative for PrP-Sc by immunohistochemistry and none showed lesions characteristic of scrapie. Forty five sheep were sampled while alive and again at necropsy or were sampled only at the time of euthanasia after clinical signs of scrapie were observed. At a minimum, brain and nictitating membrane lymphoid tissue were collected. Brain samples from all 45 sheep were positive for PrP-Sc accumulations in brain and were diagnosed with scrapie as defined by the National Veterinary Services Laboratories, Ames Iowa.

In brief, lymphoid tissue from the nictitating membrane and/or the retropharyngeal node was prepared using routine histopathologic processing techniques except that most of the tissues were decontaminated with formic acid (99% one hour) before embedding. Three micron sections were mounted on glass slides. The sections were coded and submitted to three laboratories for immunostaining. All laboratories were provided with a mixture of monoclonal antibodies F89/160.1.5 and F99/97.6.1 at a final concentration of 0.5 mg/ml each antibody. Samples were also retested at U.S. Department of Agriculture, Agricultural Research Service, Animal Disease Research Unit (USDA, ARS, ADRU). Samples at ADRU and laboratory 1 were assayed using a Ventana Medical Systems, Inc., automated immunostainer and the manufacturer's recommended reagents for horseradish peroxidase/AEC detection (ADRU) or alkaline phosphatase/Fast Red detection (laboratory 1). Laboratory 2 stained the sections using a DAKO automated immunostainer with a DAKO reagent package and laboratory 3 used an automated capillary gap immunostainer with reagents previously described (J. M. Miller et al., *Journal of Veterinary Diagnosis Investigation* 6:366–368 (1994)). Results were tabulated at ADRU.

Of the 27 sheep with no known exposure to scrapie, 26 were scored negative by all laboratories; one sample was scored positive by one laboratory (laboratory 3). Of the 47 sheep exposed to scrapie but showing no evidence of PrP-Sc in brain or lymph nodes using the immunostaining assay at ADRU, 42 were scored negative by all three laboratories. Five samples were scored positive by laboratory 3. Of the 45 sheep with scrapie, diagnosed by positive PrP-Sc immunostaining in brain, 44 were positive when re-tested at ADRU, 43 were positive at laboratories 2 and 3.

Overall, this survey demonstrated that the cocktail of monoclonal antibody F89/160.1.5 and monoclonal antibody F99/97.6.1 detects PrP-Sc in lymphoid tissues from sheep under a variety of conventional laboratory conditions. The third eyelid lymphoid tissue immunohistochemistry assay is a sensitive (93%) and specific (100%) diagnostic test for ovine scrapie. Infected sheep can be identified at approximately one third of the incubation period. The assay is also useful in studies on genetic susceptibility, transmission routes, and pathogenesis. The broad species reactivity of monoclonal antibodies F89/160.1.5 and F99/97.6.1 make this reagent cocktail suitable for immunohistochemistry and immunoblot assays of neural and extraneural tissues from all species with naturally occurring TSEs and for surveillance of related species exposed to TSEs under field conditions and in zoological gardens.

Example 2

The following example describes preparation and characterization of monoclonal antibodies which specifically bind a conserved epitope of PrP-Sc in ruminants and other animals and humans.

In brief, five mice were immunized with a KLH-conjugated synthetic peptide representing amino acids 217–233 of the ovine PrP gene product (amino acids 225–241 of the bovine PrP gene product). Antisera and hybridoma supernatants were screened by ELISA using a recombinant sheep PrP fusion protein as antigen, as described in U.S. Pat. No. 6,165,784. Cell line 99/97 produced antibodies reactive in ELISA and was selected for two rounds of cloning by limiting dilution. Hybridoma cells from the doubly cloned line (F99/97.6.1) were transferred to an in vitro artificial capillary cell culture production system. Tissue culture supernatant with monoclonal antibody F99/97.6.1 (IgG1) with a concentration of 2 to 4 mg/ml was further characterized by epitope mapping, immunoblot analysis, and immunohistochemistry.

Materials and Methods.

Antigen preparation and Monoclonal Antibody Production. The peptide $NH_2$-Cys-Ile-Thr-Gln-Tyr-Gln-Arg-Glu-Ser-Gln-Ala-Tyr-Tyr-Gln-Arg-Gly-Ala-COOH SEQ ID NO: 3, representing residues 225–241 of the bovine prion gene (Horiuchi et al., supra), was synthesized and coupled to maleimide-activated keyhole limpet hemocyanin (KLH) (Pierce Chemical Company). Five 6-week old BALB/c mice were each inoculated subcutaneously in two sites with a total of 10 µg conjugated peptide emulsified in 200 µl Freund's complete adjuvant. Two booster inoculations of 10 µg conjugated peptide in 200 µl Freund's incomplete adjuvant were administered at 14 day intervals. Sera collected by tail vein venipuncture were assayed by ELISA using a recombinant ovine PrP-C as antigen (see below). Three days before cell fusion, mice were immunized intravenously with 10 µg conjugated peptide in phosphate buffered saline (PBS) without adjuvant. Cell fusion and cloning by limiting dilution were performed following standard protocols (W. M. Yokoyama, In: J. E. Coligan (ed.), *Current Protocols in Immunology*, Wiley Intersciences, New York, p. 2.2.1–2.5.17 (1994)). Supernatants from primary and cloned hybridomas were screened by recombinant ovine PrP-C ELISA. Clone 6.1 from cell line F99/97 was selected and transferred to an artificial capillary cell culture system (CellMax, CellCo Inc.) for in vitro production of monoclonal antibody supernatant. Supernatants were collected daily and pooled. Heavy chain isotype was identified by ELISA and monoclonal antibody concentration by immunodiffusion.

Production of Recombinant Sheep PrP-C in *Escherichia Coli*. Genomic DNA was isolated from peripheral blood mononuclear cells of a Suffolk sheep. The PrP open reading frame was amplified with flanking primers (D. Westaway et al., *Genes Devel.* 8:959–969 (1994)) modified to incorporate EcoRI restriction sites:

forward primer: 5'-ATCGAATTCAAGAAGCGACCAAAAC-3' SEQ ID NO: 4, reverse primer: 5'-ATCGAATTCAGACACCACCACT-3' SEQ ID NO: 5.

The 700 bp PCR product was digested with EcoRI, purified on agarose gels, and ligated into the vector pMal-cRI. Transformation of *E. coli* strain DH5 was performed following conventional techniques. Transformants were screened by PCR of colony minipreps using the cloning primers. One positive clone (shPrP-pMal-1) was selected for large scale fusion protein expression. The fusion product ShPrP-MBP was isolated from bacterial lysates by affinity chromatography on amylose resin columns and eluted with 10 mM maltose. Fractions were screened by Western immunoblot using a rabbit antiserum to PrP peptide NH$_2$-Gly-Gln-Gly-Gly-Gly-Thr-His-Asn-Gln-Trp-Asn-Lys-Pro-Ser-Lys-COOH SEQ ID NO: 6 (R2843) (K. I. O'Rourke et al., *J. Gen. Virol.* 75:1511–1514 (1994)).

Enzyme-linked Immunosorbent Assay (ELISA). Immulon 2 plates were coated with 6.25 µg per well recombinant ShPrP-MBP fusion protein in 50 µl 0.05 M carbonate buffer, pH 9.6, overnight at 4° C. The plates were blocked with a 1:15 dilution of commercially available milk-based blocker (KPL, Gaithersburg, Md.) for one hour. 50 µl of antisera or hybridoma supernatant were incubated in each well for 30 minutes at room temperature. Plates were developed with goat anti-mouse-horseradish peroxidase and 2,2'-azino-di[3-ethyl-benzthiazoline sulfonate] (R. Fatzer et al., *Zentralbl. Veterinarmed. A.* 43:23–29 (1996)) (ABTS) (KPL, Gaithersburg, Md.). Optical density was read at 405 nm. Negative controls included sera from uninoculated mice, supernatants from isotype-matched monoclonal antibodies of irrelevant specificity, or tissue culture medium adjusted to 15% fetal calf serum. Positive control wells were incubated with rabbit anti-PrP peptide antiserum (R2843) and developed with goat anti-rabbit-HRPO and ABTS. Positive wells had OD$_{405}$ higher than two standard deviations above the mean of 4 negative control wells.

Defining the Epitope Bound by Monoclonal Antibody F99/97.6.1. An overlapping set of peptides, each with 6 amino acids, spanning Val-Glu-Gln-Met-Cys-Ile-Thr-Gln-Tyr-Gln-Arg-Glu-Ser-Gln-Ala-Tyr-Tyr-Gln-Arg-Gly-Ala-Ser-Val-Ile-Leu-Phe SEQ ID NO: 7 was synthesized on a membrane support using conventional techniques as known to those of skill in the art (Sigma-Genosys). The ability of monoclonal antibody F99/197.6.1 to bind to individual peptides was determined visually following incubation with anti-mouse-IgG-horseradish peroxidase and a chemiluminescent substrate and exposure of the filters to Kodak X-Omat film.

Source and PrP Gene Sequence of Ruminant Herbivores with Naturally Occurring TSEs. Brain tissues from 34 sheep with histopathological lesions of scrapie were tested for reactivity with monoclonal antibody F99/97.6.1 by immunohistochemistry. PrP-Sc had been detected immunohistochemically using a rabbit anti-hamster PrP polyclonal antiserum in 20 of these samples and by Western immunoblot in 6 of the 20 (J. M. Miller, *Diagn Invent.* 5:309–316 (1993)). Three sheep with no histological lesions of scrapie and no PrP-Sc detectable in Western blot analysis were used as negative controls. These tissues were provided by pathologists in veterinary medical colleges and state diagnostic laboratories or by personnel from the USDA Animal and Plant Health Inspection Service. Brain samples from 10 mule deer (*Odocoileus hemionus hemionus*) and 4 elk (*Cervus elaphus nelsoni*) with naturally occurring CWD were provided by the Colorado State Diagnostic Laboratory and the Colorado Division of Wildlife. Unstained sections from 10 cattle with BSE and 5 BSE-negative cattle were provided by the Pathobiology Laboratory, National Veterinary Services Laboratories, USDA-APHIS, Ames, Iowa. The source of paraffin blocks for these sections was Dr. Gerald Wells, Ministry of Agriculture, Fisheries and Food, Central Veterinary Laboratory, New Haw, Surrey, United Kingdom.

Frozen brain tissue for PrP genotype analysis was available from 12 of 34 scrapie-positive sheep, all 10 mule deer with CWD, and 42 CWD-affected elk. Blood samples were also available from 150 healthy mule deer and 244 healthy elk. The open reading frame of the PrP gene of the sheep was amplified by the polymerase chain reaction as described above and the polymorphic region from codons 112–240 was sequenced on both strands by automated fluorescent dye abeled dideoxy strand termination (K. I. O'Rourke et al. *Anim. Biotech.* 7:155– 162 (1996)). 100 to 800 ng of genomic DNA from mule deer or elk was amplified using species-specific primers:

forward 5'CTGCAAGAAGCGACCAAAACC SEQ ID NO: 8 reverse 5'CACAGGAGGGGAGGAGAAGAGGAT SEQ ID NO: 9 under standard conditions except that the Mg$^{+2}$ concentration was increased to 2.5 mM. PCR products were sequenced on both strands using forward primer 5'GGCTATCCACCTCAGGGAG SEQ ID NO: 10 reverse primer 5'TCACACTTGCCCCCTCTTTGGT SEQ ID NO: 11 which typically yielded sequence information on codons 106 to 224.

Immunoblot Analysis. PrP-Sc was isolated from the brain of sheep with clinical signs of scrapie by differential centrifugation from Sarkosyl buffer as described by Race et al., supra. Typically, 0.3 g of brain homogenized in 50 mM Tris-HCl, 5 mM MgCl$_2$, pH 7.4 using sonication. The homogenate was adjusted to 80 µg/ml Rnase and 20 µg/ml Dnase and incubated at 37° C. for one hour. An equal volume of 20% (w/v) Sarkosyl was added and incubated for 1.5 hours at room temperature. After centrifugation at 2,000×g for 30 minutes at 20° C., the supernatant was removed and centrifuged at 200,000×g for 2.5 hours at 20° C. Pelleted material was resuspended in 300 µl of 50 mM Tris-HCl, pH 7.4, by sonication. The suspension was adjusted to 10 µg/ml proteinase K for one hour at 37° C. to hydrolyze PrP-C. After addition of Pefabloc (Boerhinger Mannheim) to stop enzyme activity, the suspension was centrifuged at 200,000×g for 1 hour at 20° C. The pellet was boiled in 300 µl SDS sample buffer for immunoblot analysis. Varying amounts were resolved on 15% polyacrylamide gels and transferred to PVDF membranes (Millipore). The membranes were developed with 3 µg/ml F99/97.6.1, with an isotype control monoclonal antibody, or with 3 µg/ml F99/97.6.1 preabsorbed with a 100-fold molar excess of peptide Cys-Ile-Thr-Gln-Tyr-Gln-Arg-Glu-Ser-Gln-Ala-Tyr-Tyr-Gln-Arg-Gly-Ala SEQ ID NO: 3 to specifically eliminate monoclonal antibody reactivity. Bound antibody was detected with horseradish peroxidase conjugated goat anti-mouse IgG1 (Caltag Laboratories) and visualized with a chemiluminescent substrate (ECL, Amersham). Filters were exposed to film (Amersham Hyperfilm) for 20 to 120 minutes.

Immunohistochemistry. Brains were fixed in 10% buffered formalin by immersion and embedded in paraffin. One section from each block was stained with hematoxylin and eosin for routine histopathology. Additional tissue sections were mounted on were mounted on silane treated glass slides for immunohistochemistry. Sections were deparaffinized and hydrated. Sections were incubated in 99% formic acid for 5 minutes, then rinsed and neutralized with 0.1 M Tris-HCl, pH. 7.6. Sections were heat treated in an autoclave or pressure cooker at 121° C. for 20 minutes in a modified citrate buffer, pH 6.1, (DAKO TR buffer). Slides were incubated sequentially in a hydrogen-peroxide buffer to block endogenous horseradish peroxidase, monoclonal antibody cocktail F89/160.1.5 and F99/97.6.1, 3 µg/ml each in a Tris-casein diluent (32 minutes at 37° C.), biotinylated goat anti-mouse IgG (8 minutes at 37° C.), streptavidin-horseradish peroxidase (8 minutes at 37° C.), AEC/hydrogen peroxide (8 minutes 37° C.) and then counterstained with hematoxylin. Tissues were mounted in aqueous mounting medium for application of coverslips. Negative controls consisted of (1) substitution of the monoclonal antibody cocktail with a similar concentration of irrelevant monoclonal antibody of the same isotype (IgG1) and (2) incubation of the monoclonal antibody cocktail with brain and lymphoid tissue from scrapie free sheep, as indicated by histopathology and Western blot analysis.

Mule deer and Elk PrP Gene Sequences. Three alleles of the mule deer PrP sequence were identified. Alleles 138S2 (GenBank accession AF009180) and 138N1 (accession U97331) encode Ser and Asn at codon 138. Allele S1 (accession AF009181) differs from S2 by a silent mutation. Two alleles of the elk PrP gene (GenBank AF016227, AF016228) were found, encoding an M→L substitution at codon 132.

Results.

Epitope Mapping and Sequence Determination. The epitope recognized by monoclonal antibody F99/97.6.1 was mapped with a panel of overlapping peptides. Residues 220–225 (Gln-Tyr-Gln-Arg-Glu-Ser SEQ ID NO: 1) were found to be sufficient for antibody binding. This sequence is conserved in the deduced amino acid sequences of cattle mule deer, elk, goats, humans, and sheep alleles as well as in 32 species at risk for TSE. The epitope is found on the variant *C. hircus* (goat) allele (GenBank X91999) with a polymorphism in the binding site for F89/160.1.5 and the variant *O. aries* (sheep) allele with a polymorphism immediately preceding the epitope for F89/160.1.5 (cited in A. Bossers et al., *Archives of Virology* 144:829–834 (1999)).

Immunoblot Reactivity with PrP-Sc from TSE-affected Sheep. The specificity of monoclonal antibody F99/97.6.1 was evaluated by Western blot analysis of PrP-Sc preparations from sheep with natural scrapie and from normal sheep. Peptide bands with apparent molecular weights between 28–35K were detected in extracts from brain from scrapie-affected sheep. No bands were detectable in extracts from normal sheep brain or when an isotype-matched control monoclonal antibody was used or when F99/97.6.1 was absorbed with the peptide containing the epitope to which it binds.

Immunohistochemistry of Tissues from Normal and TSE-affected Ruminants. Monoclonal antibody F99/97.6.1 was further evaluated by immunohistochemistry for reactivity on formalin fixed paraffin embedded brain tissue processed routinely for histopathologic examination. All TSE-affected animals had neuropil spongiosis, intraneuronal vacuoles and gliosis within selected brainstem and midbrain nuclei, lesions diagnostic of TSE. At a minimum, the mesencephalon (at the level of the rostral colliculus) and myelencephalon (at the level of the obex) were selected for examination by immunohistochemistry. Heat treatment by autoclaving was necessary to unmask the PrP-Sc epitope binding monoclonal antibody F99/97.6.1.

Positive staining was detected in brain from sheep with natural scrapie, mule deer and elk with CWD, and cattle with BSE. Reactivity was limited to gray matter in the midbrain and brainstem, was concentrated in affected nuclei, and was present in the neuropil, and within neurons and glial cells. Most immunostaining consisted of dense granules or plaques randomly within the gray matter neuropil. Often, PrP-Sc aggregated adjacent to glial cell nuclei and accumulated in a branching pattern around glial cells identified histologically as microglia (small, oval to angular hyperchromatic nuclei without recognizable cytoplasm). There was occasional perivascular and subependymal rimming of PrP-Sc reminiscent of astroglial foot processes. Neuronal reactivity consisted of punctate immunostaining within neuronal soma or distinct rimming of neuronal soma with PrP-Sc, either within neuronal membranes or within perineuronal glial processes. Both neurons with and without intraneuronal vacuoles had PrP-Sc reactivity. No reactivity was detected in brain of unaffected sheep, deer, elk or cattle immunostained with the monoclonal antibody F99/97.6. 1 or in brain from scrapie-affected sheep or BSE-positive cattle immunostained with isotype control monoclonal antibody.

It is understood that the foregoing detailed description is given merely by way of illustration and that modification and variations may be made within, without departing from the spirit and scope of the invention.

What is claimed is:

1. A monoclonal antibody which specifically binds to a conserved epitope of prion proteins, designated as Gln-Tyr-Gln-Arg-Glu-Ser, SEQ ID NO:1, and binds PrP-Sc protein in fixed or unfixed tissue that has been treated to unmask said epitope to PrP-Sc protein and eliminate availability of a corresponding epitope of PrP-Cellular.

2. The monoclonal antibody of claim 1 wherein said monoclonal antibody binds to an epitope to which monoclonal antibody F99/97.6.1 is directed.

3. The monoclonal antibody of claim 2 designated as F99/97.6.1.

4. A hybridoma cell line, ATCC HB-12696, which produces and secretes monoclonal antibody F99/97.6.1, which specifically binds to a conserved epitope of prion proteins, designated as Gln-Tyr-Gln-Arg-Glu-Ser, SEQ ID NO: 1, and binds PrP-Sc protein in fixed or unfixed tissue that has been treated to unmask said epitope to PrP-Sc protein and eliminate availability of a corresponding epitope of PrP-Cellular.

5. A monoclonal antibody cocktail which comprises a first monoclonal antibody comprising the monoclonal antibody of claim 1 in combination with a second monoclonal antibody comprising a monoclonal antibody which specifically binds to a second conserved epitope of prion proteins, designated as Ile-His-Phe-Gly, SEO ID NO:2, and binds PrP-Sc protein in fixed or unfixed tissue that has been treated to unmask said epitope to PrP-Sc protein and eliminate availability of a corresponding epitope of PrP-Cellular.

6. The monoclonal antibody cocktail of claim 5 wherein said first monoclonal antibody binds to an epitope to which monoclonal antibody F99/97.6.1 is directed.

7. The monoclonal antibody cocktail of claim 5 wherein said second monoclonal antibody binds to an epitope to which monoclonal antibody F89/160.1.5 is directed.

8. The monoclonal antibody cocktail of claim 5 wherein said first monoclonal antibody is F99/97.6.1 and said second monoclonal antibody is F89/160.1.5 or F89/193.1.5.

9. An immunoassay method for detecting PrP-Sc protein in an animal or human which comprises:

(1) obtaining tissue from an animal or human to be tested;

(2) fixing or freezing said tissue;

(3) treating said fixed or frozen tissue to unmask epitopes to PrP-Sc and eliminate availability of a corresponding epitope of PrP-Cellular;

(4) contacting said treated tissue with monoclonal antibodies which comprises (a) monoclonal antibodies of claim 1 or (b) monoclonal antibody cocktail of claim 5, in an amount and under conditions such that said antibodies bind PrP-Sc protein if said protein is present in said tissue, and (5) detecting the presence of said bound antibodies.

10. The method of claim 9 wherein said tissue is fixed tissue and said treating is selected from the group consisting of (a) hydrated autoclaving; (b) treatment with formic acid with or without subsequent hydrated autoclaving, and (c) digestion with trypsin.

11. The method of claim 9 wherein said tissue is frozen tissue and said treating comprises treatment with proteinase K to eliminate a 35K PrP-C band and reveal characteristic multiple 28–32K bands of proteinase K-resistant PrP-Sc.

12. The method of claim 9 wherein said monoclonal antibodies bind to an epitope to which monoclonal antibody F99/97.6.1 is directed.

13. The method of claim 9 wherein said monoclonal antibody is F99/97.6.1.

14. The method of claim 9 wherein said antibody cocktail comprises a first monoclonal antibody which binds to an epitope to which monoclonal antibody F99/97.6.1 is directed and a second monoclonal antibody binds to an epitope to which monoclonal antibody F89/160.1.5 is directed.

15. The method of claim 9 wherein said first monoclonal antibody is F99/97.6.1 and said second monoclonal antibody is F89/160.1.5 or F89/193.1.5.

16. The method of claim 9, wherein said detecting comprises contacting said antibodies with a detectably labeled antimouse immunoglobulin reagent under conditions such that said reagent binds to said antibodies, and detecting said bound reagent.

17. The method of claim 9, wherein said detecting comprises:
   (a) contacting said antibodies with labeled antimouse immunoglobulin reagent under conditions such that said reagent antibody binds to said antibodies;
   (b) contacting said reagent with an enzyme-ligand complex such that said complex binds to said label on said reagent, and
   (c) detecting said enzyme-ligand complex with a chromogenic substrate.

18. The method of claim 9 wherein said animal is selected from the group consisting of ruminant livestock, cats, mink, and non-human primates.

19. The method of claim 18 wherein said ruminant livestock is selected from the group consisting of sheep, goat, cattle, mule deer and elk.

20. The method of claim 9 wherein said tissue is third eyelid-associated lymphoid tissue, brain necropsy tissue, lymph node biopsy or necropsy tissue or spleen biopsy or necropsy tissue.

* * * * *

SEQUENCE LISTING

<160> NUMBER OF SEQ ID NOS: 11

<210> SEQ ID NO 1
<211> LENGTH: 6
<212> TYPE: PRT
<213> ORGANISM: Ovis aries

<400> SEQUENCE: 1

Gln Tyr Gln Arg Glu Ser
 1               5

-continued

<210> SEQ ID NO 2
<211> LENGTH: 4
<212> TYPE: PRT
<213> ORGANISM: Bos taurus

<400> SEQUENCE: 2

Ile His Phe Gly
 1

<210> SEQ ID NO 3
<211> LENGTH: 17
<212> TYPE: PRT
<213> ORGANISM: Ovis aries

<400> SEQUENCE: 3

Cys Ile Thr Gln Tyr Gln Arg Glu Ser Gln Ala Tyr Tyr Gln Arg Gly
 1               5                  10                  15

Ala

<210> SEQ ID NO 4
<211> LENGTH: 25
<212> TYPE: DNA
<213> ORGANISM: Ovis aries

<400> SEQUENCE: 4
atcgaattca agaagcgacc aaaac                                         25

<210> SEQ ID NO 5
<211> LENGTH: 22
<212> TYPE: DNA
<213> ORGANISM: Ovis aries

<400> SEQUENCE: 5
atcgaattca gacaccacca ct                                            22

<210> SEQ ID NO 6
<211> LENGTH: 15
<212> TYPE: PRT
<213> ORGANISM: Mesocricetus auratus

<400> SEQUENCE: 6

Gly Gln Gly Gly Gly Thr His Asn Gln Trp Asn Lys Pro Ser Lys
 1               5                  10                  15

<210> SEQ ID NO 7
<211> LENGTH: 26
<212> TYPE: PRT
<213> ORGANISM: Ovis aries

<400> SEQUENCE: 7

Val Glu Gln Met Cys Ile Thr Gln Tyr Gln Arg Glu Ser Gln Ala Tyr
 1               5                  10                  15

Tyr Gln Arg Gly Ala Ser Val Ile Leu Phe
            20                  25

<210> SEQ ID NO 8
<211> LENGTH: 21
<212> TYPE: DNA
<213> ORGANISM: Odocoileus hemionus hemionus

<400> SEQUENCE: 8
ctgcaagaag cgaccaaaac c                                             21

```
<210> SEQ ID NO 9
<211> LENGTH: 24
<212> TYPE: DNA
<213> ORGANISM: Odocoileus hemionus hemionus

<400> SEQUENCE: 9
cacaggaggg gaggagaaga ggat                                              24

<210> SEQ ID NO 10
<211> LENGTH: 19
<212> TYPE: DNA
<213> ORGANISM: Odocoileus hemionus hemionus

<400> SEQUENCE: 10
ggctatccac ctcagggag                                                    19

<210> SEQ ID NO 11
<211> LENGTH: 22
<212> TYPE: DNA
<213> ORGANISM: Odocoileus hemionus hemionus

<400> SEQUENCE: 11
tcacacttgc ccctctttg gt                                                 22
```